(12) United States Patent
Leeflang et al.

(10) Patent No.: US 9,604,030 B2
(45) Date of Patent: Mar. 28, 2017

(54) VALVES AND HUBS FOR TUBULAR DEVICES AND METHODS FOR MAKING AND USING THEM

(71) Applicant: AUST Development, LLC, Palo Alto, CA (US)

(72) Inventors: Stephen A. Leeflang, Sunnyvale, CA (US); Christian S. Eversull, Palo Alto, CA (US)

(73) Assignee: AUST DEVELOPMENT, LLC, Palo Alto, CA (US)

( * ) Notice: Subject to any disclaimer, the term of this patent is extended or adjusted under 35 U.S.C. 154(b) by 314 days.

(21) Appl. No.: 13/686,771

(22) Filed: Nov. 27, 2012

(65) Prior Publication Data

US 2013/0085450 A1  Apr. 4, 2013

Related U.S. Application Data

(63) Continuation of application No. 12/581,826, filed on Oct. 19, 2009, now Pat. No. 8,317,754.

(60) Provisional application No. 61/223,352, filed on Jul. 6, 2009, provisional application No. 61/233,803, filed on Aug. 13, 2009.

(51) Int. Cl.
| | |
|---|---|
| *A61M 5/178* | (2006.01) |
| *A61M 25/00* | (2006.01) |
| *A61M 39/06* | (2006.01) |
| *B21D 28/32* | (2006.01) |
| *F16K 51/00* | (2006.01) |

(52) U.S. Cl.
CPC .... *A61M 25/0014* (2013.01); *A61M 39/0606* (2013.01); *A61M 39/0693* (2013.01); *B21D 28/32* (2013.01); *F16K 51/00* (2013.01); *A61M 2039/064* (2013.01); *A61M 2039/0633* (2013.01); *A61M 2207/00* (2013.01); *Y10T 29/49405* (2015.01); *Y10T 29/49826* (2015.01)

(58) Field of Classification Search
CPC .... A61M 2039/0633; A61M 2039/062; A61M 39/045; A61M 2039/064; A61M 2039/066; A61M 2039/0036; A61M 2039/0063
USPC ............. 604/167, 167.03, 167.04, 167.06, 604/533–537
See application file for complete search history.

(56) References Cited

U.S. PATENT DOCUMENTS

| | | | |
|---|---|---|---|
| 4,512,766 A | 4/1985 | Vailancourt | |
| 4,549,879 A | 10/1985 | Groshong | |
| 4,932,633 A * | 6/1990 | Johnson | ............ A61M 39/0606 251/149.1 |
| 4,973,319 A | 11/1990 | Melsky | |

(Continued)

*Primary Examiner* — Emily Schmidt

(74) *Attorney, Agent, or Firm* — William A English; Vista IP Law Group LLP

(57) ABSTRACT

A hub for a sheath, catheter, or other tubular device includes a first hub portion including a first hub lumen sized for receiving a medical device therethrough, and a second hub portion including a second hub lumen, the second hub portion coupled to the first hub portion such that the first and second hub lumens are aligned with one another and the first and second hub portions are spaced apart from one another to define a gap. A valve is secured within the gap between the first and second hub portions that includes a valve passage therethrough, e.g., for accommodating receiving a medical device through the first and second hub lumens into the tubular device, while providing a substantially fluid tight seal.

19 Claims, 4 Drawing Sheets

(56) References Cited

U.S. PATENT DOCUMENTS

| | | | |
|---|---|---|---|
| 5,000,745 A | | 3/1991 | Guest et al. |
| 5,092,857 A | * | 3/1992 | Fleischhacker ... A61M 39/0606 |
| | | | 137/846 |
| 5,147,332 A | | 9/1992 | Moorehead |
| 5,201,901 A | | 4/1993 | Harada et al. |
| 5,250,034 A | | 10/1993 | Appling et al. |
| 5,267,966 A | | 12/1993 | Paul |
| 5,269,764 A | * | 12/1993 | Vetter ............... A61M 39/0613 |
| | | | 251/149.1 |
| 5,304,143 A | | 4/1994 | Green et al. |
| 5,312,355 A | * | 5/1994 | Lee ................... A61M 25/0668 |
| | | | 604/160 |
| 5,350,362 A | * | 9/1994 | Stouder, Jr. ........ A61B 17/3462 |
| | | | 604/167.03 |
| 5,944,697 A | | 8/1999 | Biche |
| 6,290,668 B1 | | 9/2001 | Gregory et al. |
| 2001/0000041 A1 | | 3/2001 | Selmon et al. |
| 2006/0027270 A1 | * | 2/2006 | Truitt .................... A61M 39/02 |
| | | | 137/843 |
| 2007/0293845 A1 | * | 12/2007 | Leeflang ............... A61M 39/22 |
| | | | 604/523 |

\* cited by examiner

VALVES AND HUBS FOR TUBULAR DEVICES AND METHODS FOR MAKING AND USING THEM

This application is a continuation of application Ser. No. 12/581,826, filed Oct. 19, 2009, issuing as U.S. Pat. No. 8,317,754, which claims benefit of provisional application Ser. Nos. 61/223,352, filed Jul. 6, 2009, and 61/233,803, filed Aug. 13, 2009, the entire disclosures of which are expressly incorporated by reference herein.

FIELD OF THE INVENTION

The present invention relates generally to apparatus and methods for delivering instruments and/or agents during a medical procedure, and, more particularly, to valves and/or hubs for guide sheaths, catheters, and other tubular devices for accessing body lumens and/or delivering instruments into body lumens of a patient, and to methods for making and using them.

BACKGROUND

There are many medical procedures where a lead, catheter, electrode, and/or other medical device may be implanted into a patient's body cavity, recess, vessel, organ, and/or other body lumen. In many of these procedures, a delivery sheath, guide catheter, or other tubular member may be used to facilitate delivering the medical device, with the tubular member removed after placement of the medical device. Additionally, it may be desirable to provide a substantially fluid tight seal between the delivery sheath, guide catheter, or other tubular member and the lead, catheter, electrode, guidewire, and/or other medical device, e.g., for the purpose of hemostasis, infusion of therapeutic or diagnostic agents, and the like. However, the process of removing the tubular member from around the medical device after the medical device has been placed may be difficult and/or time consuming.

For example, a delivery sheath used to deliver a cardiac lead may not be easily removed from around the lead without disturbing the placement of the lead, which must remain in the patient. Therefore, an apparatus that may facilitate the delivery of devices, provide a seal or substantial seal, and/or facilitate removal without substantially disturbing placement of the lead and/or other device may be desirable.

SUMMARY

The present invention is directed generally to apparatus and methods for delivering instruments and/or agents during a medical procedure. More particularly, the present invention is related to valves and/or hubs for guide sheaths, catheters, and other tubular devices for accessing and/or delivering instruments into body lumens of a patient, and to methods for making and using them.

In accordance with one embodiment, a hub is provided for a sheath, catheter, or other tubular device that includes a first hub portion including a first hub lumen sized for receiving a medical device therethrough, and a second hub portion including a second hub lumen, the second hub portion coupled to the first hub portion such that the first and second hub lumens are aligned with one another and the first and second hub portions are spaced apart from one another to define a gap for receiving a valve therein.

In an exemplary embodiment, the second portion may be coupled to the first hub portion by a hub arm. For example, the hub arm may be sufficiently flexible such that the first hub portion may be directed away from the second hub portion to increase a size of the gap to accommodate inserting the valve within the gap and/or that may be resiliently biased to return towards its original shape to capture a valve within the gap. In addition or alternatively, the first and/or second valve portions may include one or more connectors for securing the valve within the gap. Optionally, the hub arm may include a side port including an opening that communicates with the second hub lumen, e.g., for delivering fluid into the second hub lumen.

Optionally, the hub may include a valve secured within the gap between the first and second hub portions. In an exemplary embodiment, the valve may include a valve passage therethrough, e.g., for accommodating receiving a medical device through the first and second hub lumens, while providing a substantially fluid tight seal. For example, the valve passage may include a bore extending partially from a first end of the valve towards a second end of the valve, and a slit that extends from the bore to the second end of the valve. The bore may have a circular or other cross-section, e.g., to accommodate introducing a medical device therethrough, and/or the slit may have opposing slit regions that are biased to close against one another, e.g., to provide a fluid-tight seal, and that are separable to accommodate receiving the medical device introduced through the bore.

In accordance with another embodiment, a valve is provided for a hub of a sheath, catheter, or other tubular device that includes a valve body including a first end, a second end, and an outer surface extending between the first and second ends; and a valve passage extending through the valve body between the first and second ends. In an exemplary embodiment, the valve passage may include a bore extending partially through the valve body from the first end towards the second end, and a slit extending through the valve body from the bore to the second end. The bore may have a circular or other cross-section, e.g., to accommodate introducing a medical device therethrough, and/or the slit may have opposing slit regions that are biased to close against one another, e.g., to provide a fluid-tight seal, and that are separable to accommodate receiving the medical device introduced through the bore. Optionally, the valve passage may include a recess within the bore that has a larger diameter or other cross-section than the bore, e.g., for receiving a lubricant and/or facilitating expansion of the valve when a medical device is inserted through the valve passage.

Optionally, the valve may include one or more connectors for securing the valve body to a hub of a tubular device, e.g., at least one of a groove and a beveled edge on the first end of the valve body. The one or more connectors may extend circumferentially around the first and second ends of the valve body, e.g., similar to corresponding connectors on the hub to which the valve is secured.

In accordance with still another embodiment, a valve is provided for a hub of a sheath, catheter, or other tubular device that includes a valve body including a first end, a second end, and one or more connectors on the first and second ends for securing the valve body to a hub of a tubular device; and a valve passage extending through the valve body between the first and second ends. The valve passage may include a bore extending partially through the valve body from the first end towards the second end, and a slit extending through the valve body from the bore to the second end. The valve body may be resiliently flexible such that a cross-section of the bore may be increased to accommodate receiving a medical device through the bore that has a cross-section larger than the bore while maintaining a substantially fluid tight seal around the medical device, and/or the slit may include opposing slit regions that open to accommodate receiving a medical device through the valve passage yet resiliently close when the medical device is removed to maintain a substantially fluid tight seal through the valve passage.

In accordance with yet another embodiment, a valve is provided for a hub of a sheath, catheter, or other tubular device that includes a valve body including a first end, a second end, and one or more connectors on the first and second ends for securing the valve body to a hub of a tubular device; a valve passage extending through the valve body between the first and second ends, the valve passage including a bore extending partially through the valve body from the first end towards the second end, and a slit extending through the valve body from the bore to the second end; and a lubricant within the bore to reduce friction when a medical device is inserted through the valve passage. The valve body may be resiliently flexible such that a cross-section of the bore may be increased to accommodate receiving a medical device through the bore that has a cross-section larger than the bore while maintaining a substantially fluid tight seal around the medical device, and/or the slit may include opposing slit regions that open to accommodate receiving a medical device through the valve passage yet resiliently close when the medical device is removed to maintain a substantially fluid tight seal through the valve passage.

In an exemplary embodiment, the bore may include a first bore region having a first diameter or other cross-section extending from the first end to an intermediate location in the valve body, and a second bore region at the intermediate location, e.g., at the bottom of the bore, that has a larger diameter or other cross-section than the first bore region, and wherein the lubricant is disposed within the second bore region.

In accordance with still another embodiment, a method is provided for making a valve for a sheath, catheter, or other tubular device that includes forming a valve body including a first end, a second end, and a bore extending partially through the valve body from the first end towards the second end; and inserting an instrument into the bore to create a slit extending from the end of the bore to the second end.

In accordance with yet another embodiment, a method is provided for making a sheath, catheter, or other tubular member that includes forming a hub including a first hub portion including a first hub lumen and a second hub portion including a second hub lumen, the second hub portion coupled to the first hub portion such that the first and second hub lumens are aligned with one another and the first and second hub portions are spaced apart from one another to define a gap; forming a valve body including a valve passage extending therethrough; and securing the valve body within the gap between the first and second hub portions such that the valve passage accommodates receiving a medical device therethrough when the medical device is introduced through the first and second hub lumens of the first and second hub portions while providing a substantially fluid tight seal. In addition, a tubular body may be attached to the second hub portion such that a lumen of the tubular body communicates with the first and second hub lumens.

In accordance with still another embodiment, a method is provided for delivering a medical device into a body lumen within a patient's body. Initially, a distal end of a tubular device may be introduced into the patient's body, the tubular device including a hub on a proximal end thereof that includes a valve secured between a proximal hub portion and a distal hub portion. The distal end of the tubular device may be positioned within a body lumen, and a medical device may be inserted through the proximal hub portion, the valve, and the distal hub portion until a distal end of the medical device is positioned within the body lumen. The proximal hub portion, valve, distal hub portion, and tubular device may be sequentially cut to remove the tubular device from around the medical device while the medical device distal end remains within the body lumen.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2A' is a cross-sectional view taken across line 2A'-2A' of FIG. 3, showing an alternative embodiment of a valve coupled to a hub that includes a relatively thin walled region aligned with a thinner region of the valve.

DETAILED DESCRIPTION OF THE EXEMPLARY EMBODIMENTS

Figure 1A:
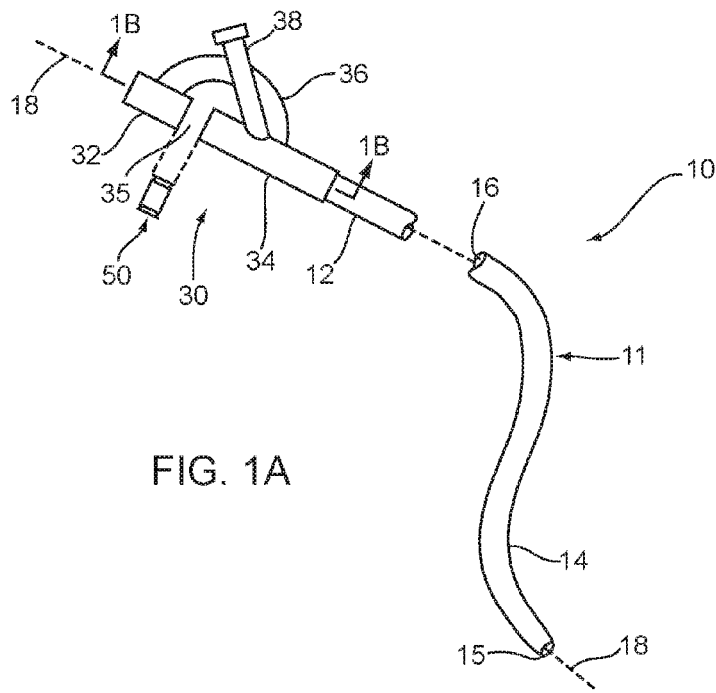
FIG. 1A is a perspective view of an exemplary embodiment of a tubular device, including a hub on its proximal end and a valve connectable to the hub.
Figure 1B:
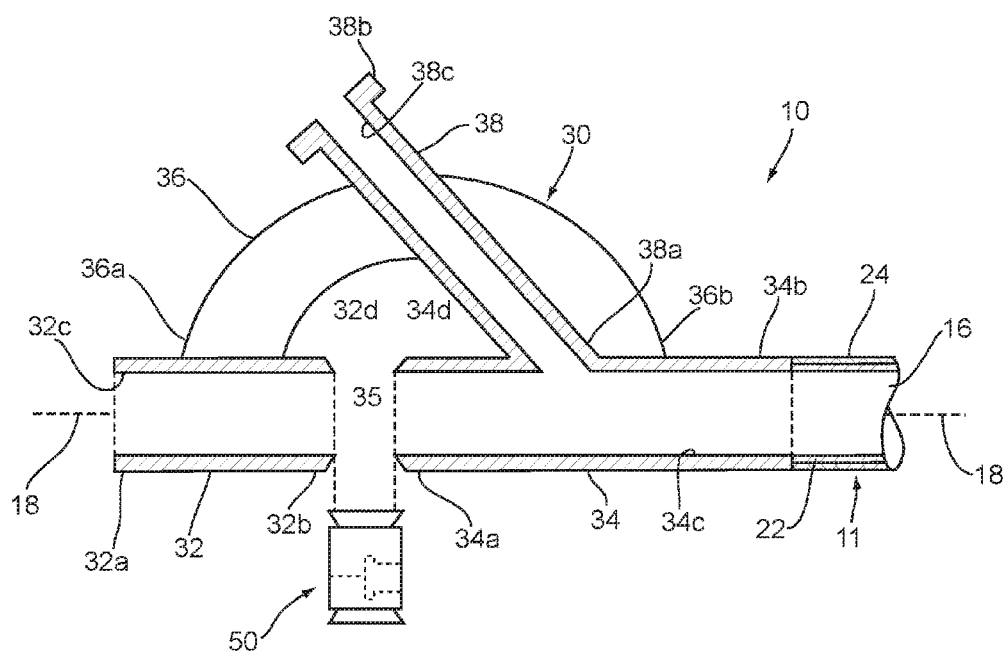
FIG. 1B is a cross-sectional view of the proximal end of the tubular device of FIG. 1A, taken along line 1B-1B, before the valve has been coupled to the hub.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 includes an elongate tubular body 11 including a proximal end 12, a distal end 14 sized for introduction into a body lumen, a lumen 16 extending between the proximal and distal ends 12, 14 along a central longitudinal axis 18, and a handle or hub 30 on the proximal end 12 including a valve 50 for allowing one or more devices to be introduced into the lumen 16. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other instrument (not shown), and/or for delivering fluids or other flowable agents or materials therethrough, as described further below.

As can be seen in FIG. 1B, the tubular body 11 may be constructed from one or more layers, e.g., an inner liner 22 surrounding the lumen 16, a reinforcing layer surrounding the inner liner (not shown), and an outer layer 24. Optionally, one or more coatings (not shown) may be applied to the inner surface of the inner liner 22. In an exemplary embodiment, a hydrophilic coating, such as Polyvinylpyrrolidone, may be sprayed or otherwise applied onto the surface of the inner liner 22 during fabrication to provide a lubricious inner surface for the lumen 16 of the tubular body 11. Exemplary materials and methods for making the tubular body 11 are disclosed in co-pending application Ser. No. 11/340,904, filed Jan. 26, 2006, Ser. No. 11/670,958, filed Feb. 2, 2007, Ser. No. 12/254,818, filed Oct. 20, 2008, and Ser. No. 12/551,540, filed Aug. 31, 2009. The entire disclosures of these references are expressly incorporated by reference herein.

The layers of the tubular body 11 may be attached to one another, e.g., by laminating, adhering, adhesive bonding, ultrasonic welding, reflowing or other heating, and the like. The construction of the tubular body 11 may be substantially uniform or may vary between the proximal and distal ends 12, 14, e.g., by varying the inner liner, 22, reinforcing layer, and/or outer layer 24 along the length of the tubular body 11. Optionally, the inner liner 22, reinforcing layer, and/or outer layer 24 may include one or more sublayers (not shown), which may vary in construction in various portions of the tubular body 11.

In one exemplary embodiment, the proximal end 12 may be substantially rigid or semi-rigid, e.g., providing sufficient column strength to allow the tubular body 11 to be pushed from the proximal end 12, while the distal end 14 may be substantially flexible or semi-rigid. Thus, the distal end 14 of the tubular body 11 may be advanced or otherwise manipulated within a patient's body from the hub 30 and/or proximal end 12 without substantial risk of buckling and/or kinking.

In exemplary embodiments, the tubular body 11 may have an outer diameter between about half and twenty millimeters (0.5-20 mm) or between about one and five millimeters (1-5 mm), and a length between about five and one hundred fifty centimeters (5-150 cm). The inner liner 22 may have a wall thickness between about 0.0001-0.01 inch (0.0025-0.25 mm) and the outer layer 24 may have a wall thickness between about 0.0005-0.2 inch (0.0127-5.08 mm).

The outer layer 24 may have a substantially homogenous construction between the proximal and distal ends 12, 14. Alternatively, the construction may vary along the length of the apparatus 10 to provide desired properties. For example, the outer layer 24 at or adjacent the proximal end 12 may be substantially rigid or semi-rigid, e.g., providing sufficient column strength to facilitate the apparatus 10 being pushed from the proximal end 12. In addition, the reinforcing layer or other material in the outer layer 24 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 24 at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 24, may have one or more transition regions along its length, transitioning from one desired construction to another. Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970. The entire disclosures of these references are expressly incorporated by reference herein.

Optionally, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Returning to FIG. 1B, an exemplary embodiment of a hub 30 is shown that includes a first or proximal hub portion 32 and a second or distal hub portion 34 coupled together by a hub arm 36. The first hub portion 32 may be an elongate tubular body including a first end 32a, a second end 32b, and a first hub lumen 32c extending therebetween. Similarly, the second hub portion 34 may be an elongate tubular body including a first end 34a, a second end 34b, and a second hub lumen 34c extending therebetween. The lengths of the first and second hub portions 32, 34 may substantially the same or different than one another, e.g., between about 0.1 and ten centimeters (0.1-10 cm).

Figure 2A:
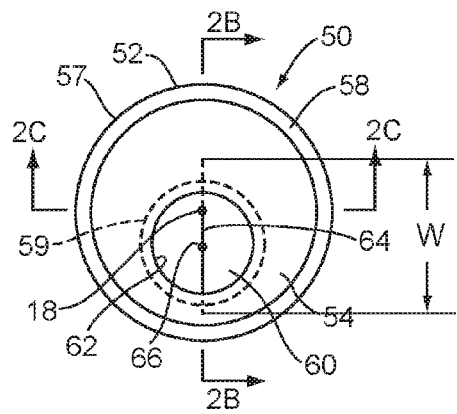
FIG. 2A is an end view of an exemplary embodiment of a valve that may be coupled to the hub of FIGS. 1A and 1B.

The hub portions 32, 34 may have a substantially uniform wall thickness. Alternatively, the thickness of the hub portions 32, 34 may vary around a circumference of the hub portions 32, 34. For example, the hub portions 32, 34 may include a relatively thin or weakened region 37 as shown in FIG. 2A', extending axially along the hub portions 32, 34, e.g., to facilitate slitting the hub 30 during use, as explained further below. In an exemplary embodiment, the relatively thin region 37 may be disposed generally opposite the hub arm 36, e.g., such that the relatively thin region 37 may be slit without substantial interference from the hub arm 36.

The first and second hub portions 32, 34 may be aligned with one another such that the first and second hub lumens 32c, 34c are also aligned with one another, e.g., concentrically around the longitudinal axis 18 of the apparatus 10. The hub lumens 32c, 34c may be sized to accommodate slidably receiving a medical device therethrough, e.g., having a diameter between about one and ten millimeters (1-10 mm), which may allow introduction of a medical device through the hub 30 into the tubular body 11, as explained further below. Alternatively, the hub portions 32, 34 and/or hub lumens 32c, 34c may have an elliptical or other cross-section rather than a circular cross-section, if desired.

The first end 32a of the first hub portion 32 may include a transition and/or other features to facilitate introducing a medical device into the first hub lumen 32c. For example, the first end 32a may include a tapered wall (not shown) communicating with the first hub lumen 32c. The second end 34b of the second hub portion 34 may include one or more connectors (not shown) for attaching the tubular body 11 to the hub 30. For example, the second end 34b may include one or more tabs, slots, threads, and the like (not shown) that may be engaged with complementary slots, tabs, threads, and the like (also not shown) on the proximal end 12 of the tubular body 11. In addition or alternatively, the second end 34b may be engaged with the proximal end 12 by an interference fit, may be attached by bonding with adhesive, fusing, sonic welding, heat bonding, reflowing, insert molding, and the like, if desired.

As shown in FIG. 1B, the arm 36 may include a first end 36a attached to the first hub portion 32 and a second end 36b attached to the second hub portion 34, thereby maintaining the first and second hub portions 32, 34 spaced apart from one another to define a gap 35. In an exemplary embodiment, the hub portions 32, 34 may be spaced apart such that the gap 35 has an axial length (substantially parallel to the longitudinal axis 18) or other size, e.g., between about one and ten millimeters (1-10 mm). The arm 36 may be sufficiently flexible such that the first hub portion 32 may be directed away from the second hub portion 34 to increase an axial length or other size of the gap 35, e.g., to accommodate inserting the valve 50 within the gap 35, as explained further below.

For example, during manufacturing or otherwise before use, the hub portions 32, 34 may be directed slightly apart from one another to increase the length of the gap 35 while a valve 50 is inserted within the gap 35. When the hub portions 32, 34 are released, the hub portions 32, 34 may return to their original position, e.g., engaging or otherwise capturing the valve 50 within the gap 35, as explained further below. As shown, the arm 36 may have an arcuate shape, e.g., a curved shape having a substantially uniform or varying radius of curvature between the first and second ends 36a, 36b. The shape and/or material of the arm 36 may accommodate bending the arm 36 open slightly when the hub portions 32, 34 are directed apart, and automatically returning the arm 36 to its original shape when the hub portions 32, 34 are released, thereby returning the hub portions 32, 34 to their original relative positions. Alternatively, the arm 36 may have other shapes, which may be flexible to accommodate inserting the valve 50 within the gap 35. Alternatively, the arm 36 may be substantially rigid and/or the gap 35 substantially fixed. In addition or in a further alternative, the valve 50 may be inserted into the gap 35 by temporarily deforming the valve 50. The valve 50 may then return to its original shape, thereafter being engaged within the gap 35. The valve 50 may be introduced into the gap 35 from the side or through the hub lumen 32c or 34c of the hub portion 32 or 34. Optionally, if desired, the arm 36 may have other shapes adapted to enable secure gripping of the arm 36 for manipulation of the apparatus 10, including, for example, advancing, retracting or rotating within a body lumen, and/or removal of the apparatus 10 by slitting.

Optionally, the second end 32b of the first hub portion 32 and/or the first end 34a of the second hub portion 34 may include one or more connectors (not shown) for cooperating with complementary connectors on the valve 50 and/or for otherwise engaging the valve 50 captured within the gap 35. For example, the ends 32b and/or 34a may include one or more tabs, slots, threads, features and the like (not shown), which may be engaged with complementary slots, tabs, threads, features and the like (also not shown) on the valve 50. Alternatively, or in addition, as shown in FIG. 1B, the ends 32b, 34a may include beveled edges 32d, 34d extending around a circumference of the ends 32b, 34a that may be captured in corresponding slots 58 in the valve 50, as explained further below.

The hub 30 may also include one or more side ports, e.g., a first side port 38 communicating with the lumen 16. Optionally, one or more additional side ports (not shown) may be provided on the hub 30 communicating with respective lumen(s), e.g., if the tubular body 11 includes an inflation lumen for a balloon on the distal end 14 (also not shown). The side port 38 generally includes a tubular body including a first end 38a coupled to the second hub portion 34, a second end 38b including a connector (not shown), and a lumen 38c extending from the second end 38b to the first end 38a and communicating with the second hub lumen 34c. In an exemplary embodiment, the connector on the second end 38b may include a luer lock connector, a hemostatic seal, and the like, e.g., for coupling a source of fluid, inflation media, and/or vacuum to the side port 38.

Optionally, the hub 30 may include one or more other connectors, e.g., luer lock connectors, electrical connectors, and the like (not shown), for connecting other devices (not shown) to the apparatus 10, such as syringes, displays, controllers, and the like (also not shown). In addition, the hub 30 may include one or more actuators, such as sliders, buttons, switches, and the like, e.g., for activating and/or manipulating components (also not shown) on the distal end 14 or otherwise operating the apparatus 10.

Multiple components of the hub 30 may be integrally formed together as a single piece or may be formed separately and then attached together to provide the hub 30. For example, the hub portions 32, 34, arm 36, and side port 38 may be formed as a single piece, e.g., by injection molding, casting, and the like. Alternatively, the hub portions 32, 34 and side port 38 may be formed separately, e.g., by extrusion, injection molding, casting, and the like, and attached to the hub arm 36 and/or to each other, as desired, e.g., using cooperating connectors (not shown), bonding with adhesive, fusing, sonic welding, heat bonding, reflowing, insert molding, and the like. The hub 30 and/or its components may be formed from plastic, metal, or composite materials, as desired, such as nylon, PEBAX, PTFE, HDPE, and the like.

Figure 2B:
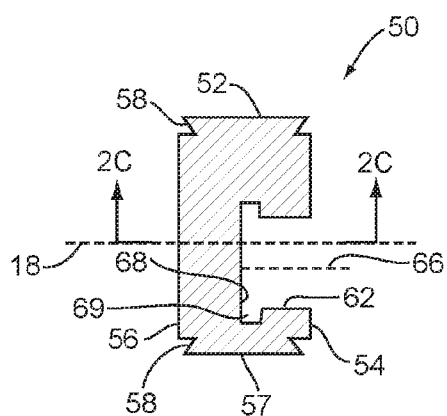
FIG. 2B is a cross-sectional side view of the valve of FIG. 2A, taken along line 2B-2B.
Figure 2C:
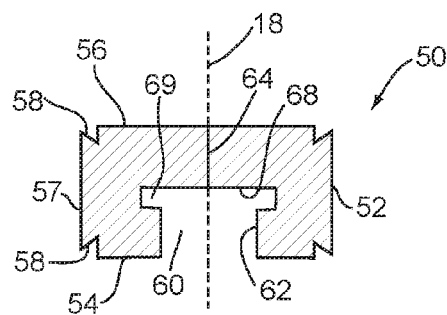
FIG. 2C is a cross-sectional top view of the valve of FIGS. 2A and 2B, taken along line 2C-2C.

Turning to FIGS. 2A-2C, an exemplary embodiment of a valve 50 is shown that generally includes a valve body 52 including a proximal or first end 54, a distal or second end 56, an outer surface 57 extending between the first and second ends 54, 56, and a valve passage 60 extending between the first and second ends 54, 56. As shown, the valve passage 60 includes a bore 62 and a slit 64 that are formed adjacent one another within the valve body 52. For example, the bore 62 may extend from the first end 54 partially through the valve body 52 to an intermediate region such that the bore 62 defines a bottom surface 68, and the slit 64 may extend from the bore 62, e.g., from the bottom surface 68, to the second end 56 of the valve body 52. As explained further below, the bore 62 may allow the valve 50 to provide a substantially fluid-tight seal when a medical device (not shown) is inserted into the valve passage 60, while the slit 64 may provide a fluid-tight seal when the valve passage 60 is empty (i.e., without a medical device inserted into the valve passage 60).

Optionally, the valve passage 60 may also include a recess 69, e.g., at the bottom 68 of the bore 62. For example, the recess 69 may extend circumferentially around the bore 62 adjacent the bottom 68 to define an annular pocket within the valve passage 60 that has a diameter or other cross-section that is larger than the bore 62. For example, with the valve body 52 in a relaxed state (e.g., without a medical device, tool, or other instrument inserted into the bore 62), the bore 62 may have a diameter between about 0.25 and eight millimeters (0.25-8 mm), and the recess 69 may a diameter larger than the bore 62 between about 0.3 and nine millimeters (0.3-9 mm). Alternatively, one or more discrete recesses or pockets (not shown) may be provided within the bore 62, e.g., spaced apart from one another circumferentially around the bore 62 and/or axially along the bore 62, if desired. Such recess(es) may accommodate providing a lubricant within the valve passage 60, e.g., to reduce friction or otherwise facilitate introducing a medical device, tool, or other instrument into the valve passage 60, as explained further below. In addition or alternatively, the recess 69 may facilitate expansion of the bore 62, e.g., when a medical device, tool, or other instrument is inserted into the bore 62, also as explained further below. In addition or alternatively, the recess 69 may be adapted decrease or stop propagation of tears during expansion of the bore 62 or slit 64, e.g., when a medical device, tool, or other instrument is inserted through the valve body 52, as described further below.

As best seen in FIGS. 2B and 2C, the valve body 52 may be formed such that both the outer surface 57 and bore 62 extend substantially parallel to the longitudinal axis 18. However, as best seen in FIGS. 2A and 2B, a central axis 66 of the bore 62 may be offset from the longitudinal axis 18, e.g., such that the bore 62 is closer to the outer surface 57 of the valve body 52 on one side than the opposite side. Thus, a side wall region of the valve body 52 adjacent the bore 62 may be thinner on one side of the valve body 52 than other side wall regions, which may facilitate slitting the valve 50 during use, as explained further below.

The bore 62 may be sized appropriately to allow a medical device (not shown) to pass freely through the bore 62 without substantial frictional resistance and/or to provide a seal around the medical device to prevent substantial fluid leakage when the medical device is passed through the bore 62. Optionally, the valve body 52 may be resiliently flexible such that the bore 62 may be dilated or otherwise expanded when a medical device is inserted into the bore 62 and may resiliently return to its original size when the medical device is removed. Thus, the bore 62 may expand to accommodate a medical device having a larger cross-section than the bore 62 with the valve body 52 in the relaxed state. For example, with the valve body 52 in the relaxed state (e.g., without a medical device inserted into the bore 62), the bore 62 may have a diameter between about 0.25 and eight millimeters (0.25-8 mm), but may be expandable to larger diameters, e.g., between about 0.35 and ten millimeters (0.35-10 mm).

The slit 64 may also extend substantially parallel to the longitudinal axis 18 from the bottom 68 of the bore 62 to the second end 56 of the valve body 52, as best seen in FIG. 2C. Alternatively, two or more intersecting slits (not shown) may extend from the bottom 68 of the bore 62 to the second end 56 of the valve body 52, for example in an intersecting cross pattern (not shown). As best seen in FIG. 2A, the slit 64 may have a width "W" at least as long as the diameter of the bore 62, and, optionally, may have a length greater than the diameter of the bore 62, e.g., between about 0.25 and eight millimeters (0.25-8 mm). The width of the slit 64 may be substantially uniform between the bottom 68 of the bore 62 and the second end 56 of the valve body 52 or may vary along its length. For example, the width of the slit 64 may be greater adjacent the bore 62 than at the second end 56 of the valve body 52, if desired.

The width of the slit 64 may be sufficient to allow opposing regions of the valve body 52 on either side of the slit 64 to be directed away from one another to accommodate receiving a medical device through the valve passage without substantial risk of the valve body 52 tearing uncontrollably. Thus, the valve body 52 may be resiliently flexible such that the opposing slit regions may expand when a medical device is inserted through the slit 64, yet resiliently close when the medical device is removed to maintain a substantially fluid tight seal through the valve passage 60.

Alternatively, the slit 64 may provide a relatively small passage to guide a medical device from the bore 62 through the valve body 52 to the second end 56, e.g., with the slit 64 providing a preferential tear line through the valve body 52 as the medical device is inserted therethrough. In another alternative, the valve body 52 may include features, such as the recess 69, which may decrease or stop propagation of tears initiated as a medical device is inserted therethrough.

Figure 2D:
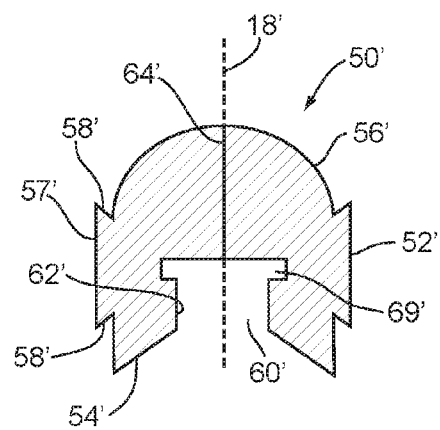
FIG. 2D is a cross-sectional top view of an alternative embodiment of the valve of FIGS. 2A-2C.

Optionally, the valve body 52 may include one or more additional features. For example, as shown in FIG. 2D, an alternative valve body 52' is shown that includes a first end 54' that is at least partially tapered, e.g., to facilitate introduction of a medical device therethrough and/or into the bore 62.' As shown, the first end 54' includes a surface 55' that tapers from the first end 54' into the bore 62,' which may guide a medical device introduced into a hub (not shown) towards the bore 62.' For example, if the medical device has a diameter smaller than the first hub lumen 32c (not shown, see, e.g., FIG. 3), the tapered surface 55' may facilitate guiding the medical device inserted into the first hub lumen 32c through the valve 50' and into the second hub lumen 34c.

Figure 3:
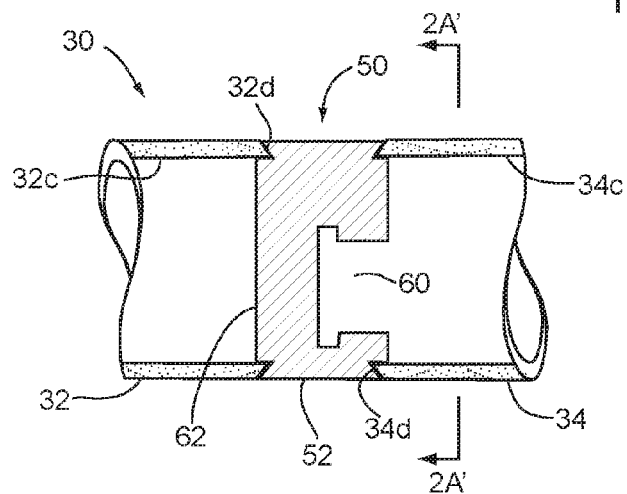
FIG. 3 is a cross-sectional detail of the hub of FIGS. 1A and 1B, showing the valve of FIGS. 2A-2C coupled to the hub.
Figure 2A:
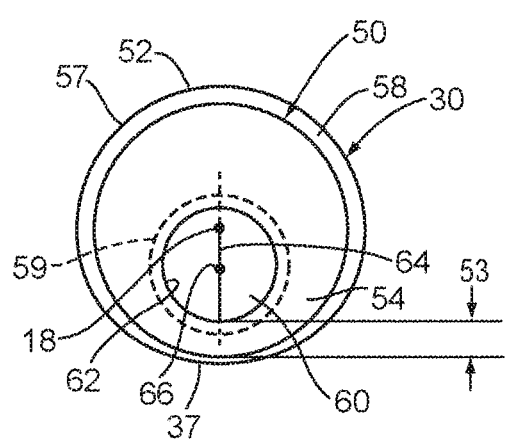

In addition or alternatively, the valve body 52' may include a convex or otherwise shaped second end 56' that includes less material towards the outer surface 57' of the valve body 52' than towards the central longitudinal axis 18.' Such a shape may facilitate directing opposing slit regions away from one another when a medical device is inserted into the slit 64' since there is less material to bunch up adjacent the wall of the second hub portion 34 (not shown, see, e.g., FIG. 3). Such a shape may also distribute forces within the valve body 52' when a medical device is inserted into the slit 64' to prevent undesired tearing of the valve body 52.' Such a shape may also facilitate sealing the valve when no medical device is inserted into the slit 64' and pressure is applied to the second end 56.'

Returning to FIGS. 2A-2C, the valve body 52 may be formed from an elastomeric material, such as silicone, chronoprene, isoprene, santoprene, and the like. In one embodiment, the valve body 52 may be integrally formed as a single piece, e.g., by injection molding, casting, and the like. For example, with continued reference to FIG. 2A, the valve body 52, including connectors 58, bore 62, and recess 69, may be integrally formed, e.g., by injection molding, casting, and the like. Alternatively, the valve body 52 may be formed as a solid body and the connectors 58, bore 62, and/or recess 69 may be formed into the solid body, e.g., by cutting, machining, and the like.

Figure 4A:
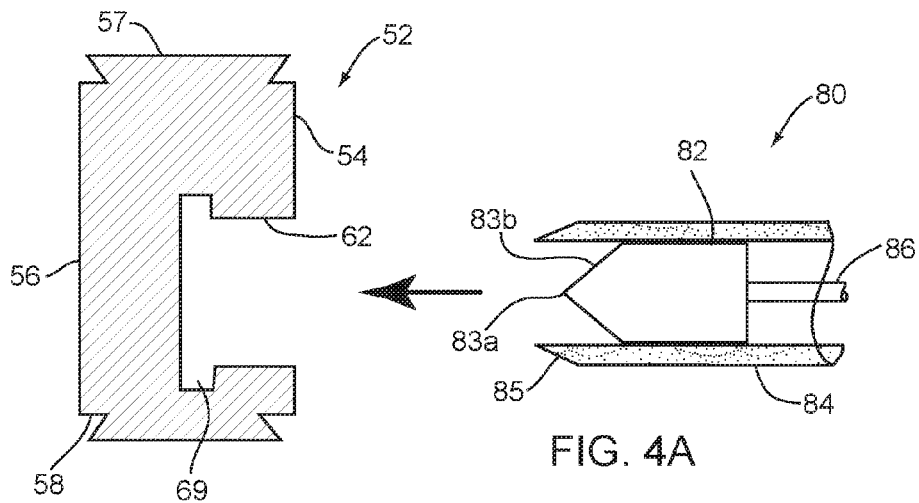
FIGS. 4A-4C are cross-sectional views of a valve body showing a method for making a slit through the valve body to create the valve of FIGS. 2A-2C.
Figure 4B:
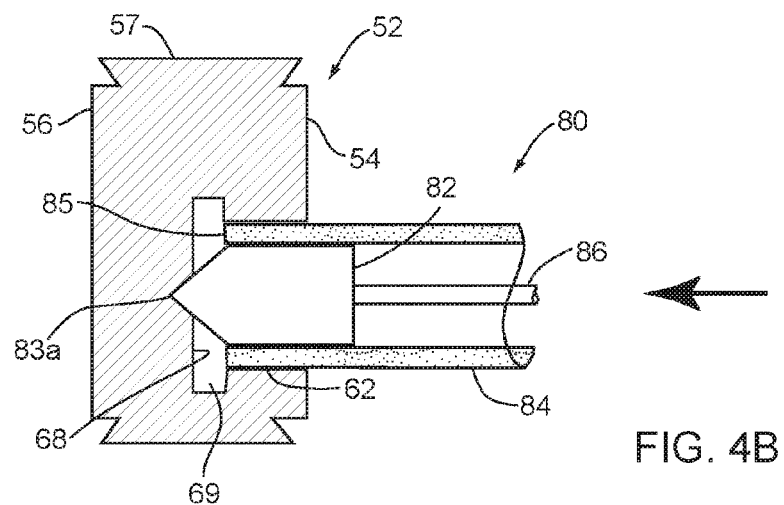
Figure 4C:
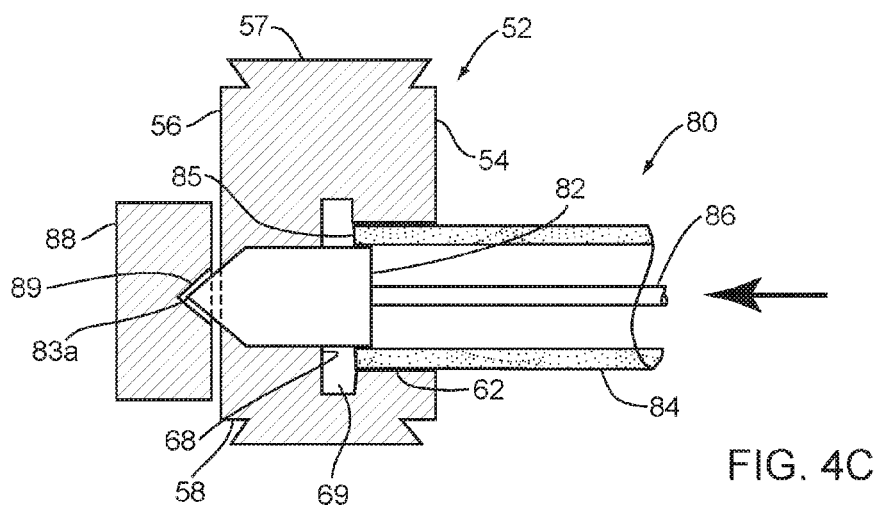

Once the valve body 52 including the bore 62 are formed, the slit 64 may be formed in the valve body 52, e.g., to complete the valve passage 60. Turning to FIGS. 4A-4C, an exemplary method is shown for forming the slit 64 in the valve body 52 of FIGS. 2A-2C. Initially, as shown, a valve body 52 may be provided including a bore 62 (and optionally recess 69) formed therein, as described above. A tool 80 may be provided to cut or otherwise penetrate through the valve body 52 to create the slit 64. For example, the tool 80 may include a blade or other cutting element 82 for mechanically cutting or slicing through the valve body 52, although alternatively other devices may be used, for example, a heated blade, wire, or other element that may melt through the valve body 52, e.g., in addition to or instead of mechanically cutting the valve body 52.

As shown in FIGS. 4A-4C, the tool 82 includes a blade or other mechanical cutting element 82, e.g., having a width corresponding the desired width of the slit 64 to be formed. In addition or alternatively, the cutting element 82 may have a relatively thin thickness, e.g., between about 0.05 and 0.75 millimeter (0.05-0.75 mm), to facilitate advancing the cutting element 82 through the material of the valve body 52 with minimal friction and/or risk of tearing the valve body 52. As shown, the cutting element 82 may include a sharpened tip 83a and/or one or more sharpened edges 83b (two shown), which may facilitate cutting into the material of the valve body 52.

Optionally, the cutting element 82 may be deployable from a sleeve or other assembly 84, e.g., such that the cutting element 82 may be initially provided within the sleeve 84 and may be advanced from and/or retracted into the sleeve 84 when desired. For example, the tool 80 may include a handle (not shown) coupled to a proximal end of the sleeve 84 that includes an actuator (also not shown) coupled to a shaft or other actuator member 86 carrying the cutting element 82.

Optionally, as shown in FIG. 4C, the tool 80 may include a rigid stop 88, which may be placed opposite the sleeve 84 and cutting element 82 to facilitate penetrating the cutting element 82 sufficiently into the valve body 52. For example, the stop 88 may include a slot or other recess 89 that may be sized to receive at least the tip 83a of the cutting element 82 therein, e.g., to ensure that the cutting element 82 penetrates a sufficient depth into or through the valve body, as described further below.

The sleeve 84 may include a distal end 85 which may be tapered, as shown in FIG. 4A, e.g., to provide a transition that facilitates advancing the sleeve 84 at least partially into the bore 62 of the valve body 52. Alternatively, the distal end 85 may be blunt, e.g., as shown in FIGS. 4B and 4C, or otherwise shaped. The distal end 85 of the sleeve 84 may have a diameter or other cross-section smaller than the bore 62 in its relaxed state, e.g., such that the distal end 85 may be inserted into the bore 62 without deforming the valve body 52, e.g., before deploying the cutting element 82. Alternatively, the distal end 85 of the sleeve 84 may be larger than the bore 62, e.g., such that the bore 62 may be expanded when the sleeve 84 is inserted therein, as shown in FIGS. 4B and 4C. In this alternative, the cutting element 82 may have a width greater than the diameter of the bore 62 in the relaxed state, e.g., to form a slit 64 having a width greater than the diameter of the bore 62.

Turning to FIG. 4A, the cutting element 82 is shown retracted within the sleeve 84 and the sleeve 84 is directed towards the valve body 50, i.e., into the bore 62. As shown in FIG. 4B, the distal end 85 of the sleeve 84 has been inserted into the bore 62, e.g., until the distal end 85 contacts or is immediately adjacent the bottom 68 of the bore 62. As shown, the bore 62 has been expanded by the distal end 85 of the sleeve 84 to a diameter approaching the diameter of the recess 69, although alternatively, the bore 62 may be expanded further, which may also expand the recess 69.

Turning to FIG. 4C, the cutting element 82 has been advanced from the sleeve 84 such that the distal tip 83a penetrates through the bottom 68 of the bore 62 and through the valve body 52 and at least partially out through the second end 56. Thus, the cutting element 82 has created a slit 64 that extends from the bottom 68 of the bore 62 through to the second end 56 of the valve body 52. As shown, the distal tip 83a of the cutting element 82 has exited the valve body 52 and entered the slot 89 in the stop 88. The stop 88 may also prevent deformation of the valve body 52 when the cutting element 82 is advanced through the second end 56, thereby reducing the risk of tearing or otherwise damaging the valve body 52.

The cutting element 82 may be retracted back into the sleeve 84 and the sleeve 84 removed from the bore 62, thereby providing a slit 64 extending through the valve body 52, as shown in FIGS. 2A-2C. In an alternative embodiment, the cutting element 82 or other tool may be used to create the slit 64 by penetrating the second end 56 of the valve body 52, e.g., through the bottom 68 of the bore 62, if desired, rather than through the bore 62 from the first end 54 of the valve body 52.

Optionally, lubricant or other material may be introduced into the bore 62, e.g., into the recess 69. Any additional features may be formed in the valve body 52, if desired, to create the final valve 50. The valve 50 may thereafter be incorporated into a hub or other apparatus.

Returning to FIGS. 1A and 1B, any of the valves herein, such as valve 50 or 50,' may be secured to a hub 30 of an apparatus 10, e.g., a sheath, catheter, or other tubular member, to accommodate receiving one or more devices, e.g., a catheter, lead, guidewire or other medical device (not shown), through the hub 30 and into the lumen 16 of the tubular body 11, while providing a substantially fluid-tight seal. For example, as described above, a hub 30 may be formed that includes a first hub portion 32 and a second hub portion 34 coupled together by hub arm 36 such that first and second hub lumens 32c, 34c of the hub portions 32, 34 are aligned with one another and the hub portions 32, 34 are spaced apart from one another to define a gap 35, as best seen in FIG. 1B.

A valve 50 may be selected and secured to the hub 30 within the gap 35. For example, using any of the methods described above, a valve 50 may be formed that includes a valve body 52 including a valve passage 60 extending therethrough. During manufacturing or final assembly, the valve body 52 may be secured within the gap 35 between the first and second hub portions 32, 34 such that the valve passage 60 is aligned with the hub lumens 32c, 34c, e.g., to accommodate receiving a medical device through the hub 30 into the tubular body 11 while providing a substantially fluid tight seal.

Alternatively, it may be possible to provide a plurality of valves to an end user separate from a hub 30 such that the user may select a desired valve for use during a particular procedure. For example, different valves having different configurations, e.g., different sizes of valve passage 50, different material properties, and the like, may be provided to a user, and the user may simply select a desired configuration from the available valves and secure the valve to the hub 30.

For example, as described above, the first and second hub portions 32, 34 may be directed away from one another, e.g., by bending the hub arm 36 slightly, to increate a length of the gap 35, thereby providing additional space to insert the valve body 52 between the hub portions 32, 34. The valve body 52 may then be inserted within the gap 35 between the hub portions 32, 34, and the hub portions 32, 34 may be directed back towards one another to capture the valve body 52 between the hub portions 32, 34. In one embodiment, the hub portions 32, 34 may be directed towards one another simply by releasing the hub arm 36 and/or the hub portions 32, 34, whereupon the hub arm 36 may resiliently return towards its original shape, thereby directing the hub portions 32, 34 towards one another.

The resulting interference fit alone may be sufficient to secure the valve 50 within the gap 35. For example, as shown in FIG. 3, when the valve 50 is captured between the hub portions 32, 34, the beveled edges 32d, 34d may engage the slots 58 in the valve body 52, thereby substantially securing the valve 50 within the gap 35. If desired, the valve body 52 may in addition or alternatively be secured using other methods, e.g., at least one of bonding with adhesive, welding, insertion molding, or fusing the valve body 52 to the first and/or second hub portions 32, 34, surrounding bands (not shown), and/or other connectors. Where adhesive is used to secure the valve 50 within the gap 35, the valve body 52 and/or the hub portions 32, 34 may include recesses, channels, or other features (not shown) designed to receive and/or distribute adhesive at the interface between the hub portions 32, 34 and the valve body 52.

If the hub portions 32, 34 include relatively thin walled regions, e.g., thin walled region 37 shown in FIG. 2A', and/or the valve 50 includes a valve passage offset towards one side of the valve body 52, one or more connectors or alignment features may be provided on the valve 50 and/or hub portions 32, 34 to ensure that the valve 50 is properly oriented when captured within the gap 35. For example, one of the hub portions 32, 34 and the valve body 52 may include one or more tabs (not shown) that may be received in corresponding one or more slots (also not shown) in the other of the hub portions 32, 34 and the valve body 52 only when the valve 50 is oriented properly relative to the hub portions 32, 34. Such alignment features may ensure that relatively thin walled regions 37 of the hub portions 32, 34 are aligned with the thinner region 53 of the valve body 52, as shown in FIG. 2A', which may facilitate slitting the hub 30 after use during a procedure, as described further below.

In an alternative embodiment, one of the first and second hub portions 32, 34 may be provided separate from the hub arm 36, e.g., during manufacturing, and the valve 50 may be secured to the hub 30 before attaching the separate hub portion. For example, with reference to FIG. 1B, the hub 30 may be formed with only the second hub portion 34 and the side port 38 attached to the hub arm 36. The valve body 52 may be secured to the first end 34a of the second hub portion 34, e.g., by bonding with adhesive, welding or fusing, one or more connectors, and the like. The first hub portion 32 may then be attached to the hub 30 and/or the valve 50. For example, the first hub portion 32 may be attached to the first end 36a of the hub arm 36, e.g., using the methods described above, and the second end 32b of the first hub portion 32 may be attached to the valve body 52, e.g., similar to the second hub portion 34.

Once the valve 50 is secured or otherwise captured within the gap 35 of the hub 30, the hub 30 may be incorporated into an apparatus 10, as shown in FIG. 1A. For example, the second end 34b of the second hub portion 34 may be attached to the proximal end 12 of the tubular body 11, e.g., after (or optionally before) assembling the hub 30. The resulting apparatus 10 may be sterilized and/or packaged, as desired, and provide to a user, or the apparatus 10 without the valve 50 may be provided to a user for assembly immediately before a procedure, e.g., as described above.

During use, the apparatus 10 may be used for delivering a medical device into a body lumen within a patient's body, e.g., a lead, catheter, and the like, into a patient's vasculature or other body lumen, as described above. For example, a distal end 14 of the tubular body 11 may be introduced into a patient's vasculature with the hub 30 and valve 50 remaining outside the patient's body. The tubular body 11 may be advanced through the patient's vasculature, e.g., to position the distal end 14 and a desired location, e.g., a coronary vein within the patient's heart or other body lumen. A medical device, e.g., a pacing or other electrical lead (not shown), may be inserted through the first hub portion 32, the valve 50, and the second hub portion 34 and into the tubular body 11 until a distal end of the medical device is advanced into the body lumen, e.g., exiting or remaining within the distal end 14 of the tubular body 11.

The apparatus 10 may then be removed to leave the medical device implanted within the patient's body. The configuration of the hub 30 may facilitate removing the apparatus 10 from around the medical device without substantial risk of dislodging or otherwise moving the medical device. For example, cardiac leads often include relatively large proximal hubs, e.g., including electrical connectors and the like, which may prevent the apparatus 10 from being removed over the hub. Instead, a slitter or other tool (not shown) may be used to slit the hub 30, valve, and tubular body 11 to open the apparatus 10 and allow easy removal despite a large hub or other obstacle.

For example, a slitter may be used sequentially cut the first hub portion 32, the valve body 52, the second hub portion 34, and the tubular body 11. If the hub portions 32, 34 and/or valve body 52 include relatively thin walled regions aligned with one another, the regions may be identified, e.g., by a colored line, a recess (not shown) in the first end 32a of the first hub portion 32, and the like, to facilitate identification by the user. Optionally, the tubular body 11 may include a tear-away or other weakened region that may be aligned with the relatively thin walled regions of the hub 30, which may facilitate slitting or may simply propagate separation of the region along the length of the tubular body 11 with or without use of a slitter or other tool.

Because the valve body 52 is slit separately from the hub portions 32, 34, the user only needs to slit one layer of material, which may facilitate slitting the hub 30, e.g., compared to hubs with valves disposed concentrically within a tubular hub. Simultaneously slitting such a concentric valve and tubular hub may require greater force, since multiple layers of dissimilar materials must be slit together, which increases the risk of moving the medical device being implanted.

With reference to FIGS. 2A-2C, another advantage of the valves described herein is that the valve body 52 may have an overall length that is substantially shorter than conventional valves. This relatively short length may reduce friction between the valve 50 and medical device inserted through the valve passage 60 since there is less surface area to contact the medical device. This is particularly useful when the valve body 52 is formed from materials, such as silicone, which may be tacky.

With further reference to FIGS. 2A-2C, still another advantage of the valves described herein is that the recess 69 at the bottom of the bore 62 within the valve body 52 may limit propagation of a tear when a medical device is inserted through the valve passage 60 of the valve 50. For example, if a medical device is inserted through the bore 62 into the slit 64 and causes the slit 64 to tear further into the valve body 52, the recess 69 may provide a negative cavity creating a "rip stop" that may prevent the tear from propagating towards the first end 54 of the valve body 52. If the valve body 52 surrounding the bore 62 were to tear, there would be substantially increased risk of leaking around the medical device inserted through the valve passage 60. Similarly, any tear that is created by over-expansion of the bore 62 may be prevented from propagating towards the valve body 52 surrounding the slit 64 due to the rip stop provided by the recess 69.

With further reference to FIGS. 2A-2C, still another advantage of valves described herein is that because such valves are not disposed concentrically within a tubular hub, they may expand unconstrained to accommodate insertion of a medical device. As a result, the valve 50, including the bore 62, may be sized to seal on a relatively small device, such as a guidewire, while accommodating passage of a relatively larger device, such as a lead or catheter, without causing excessive friction during passage of the relatively larger device.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A valve for a hub of a sheath, catheter, or other tubular device, comprising:
    a valve body comprising a first end terminating at a first end wall, a second end opposite the first end and terminating at a second end wall, an outer surface extending between the first and second end walls, and a longitudinal axis extending between the first and second end walls disposed centrally and concentrically relative to the outer surface; and
    a valve passage extending through the valve body between the first and second end walls, the valve passage comprising a bore extending partially from the first end wall partially towards the second end wall to a bottom surface at an intermediate region and defining a central bore axis that is substantially parallel to and offset from the central longitudinal axis such that, at the first end wall, one side of the bore is closer to the outer surface of the valve body than the opposite side of the bore, the bore defining a side wall extending substantially parallel to the central bore axis from the first end wall towards the bottom surface, the valve passage further comprising a slit extending through the valve body from the bottom surface to the second end wall,
    wherein the valve passage further comprises a recess within the bore that has a larger cross-section than the bore.

2. The valve of claim 1, wherein the slit has a length that extends substantially parallel to the central longitudinal axis between the bottom surface and the second end wall and a width perpendicular to the central longitudinal axis that extends partially between the one side of the outer surface of the valve body and the opposite side of the outer surface.

3. The valve of claim 1, wherein the valve body is resiliently flexible such that a cross-section of the bore may be increased to accommodate receiving a medical device through the bore that has a cross-section larger than the bore while maintaining a substantially fluid tight seal around the medical device.

4. The valve of claim 3, wherein the valve body is resiliently flexible such that the slit may open to accommodate receiving a medical device through the valve passage yet resiliently close when the medical device is removed to maintain a substantially fluid tight seal through the valve passage.

5. The valve of claim 1, further comprising one or more connectors for securing the valve body to a hub of a tubular device.

6. The valve of claim 5, wherein the one or more connectors comprise at least one of a groove and a beveled edge on the first end of the valve body.

7. The valve of claim 5, wherein the one or more connectors extend circumferentially around the first and second ends of the valve body.

8. The valve of claim 1, wherein the sidewall of the bore defines a cylindrical passage that has a diameter smaller than the outer surface of the valve body and sized to provide a seal around a medical device inserted through the valve passage.

9. A hub for a sheath, catheter, or other tubular device, comprising:
    a hub member comprising a first hub end, a second hub end connectable to an elongate tubular member sized for introduction into a patient's body, and a lumen extending therebetween for receiving a medical device introduced into the first hub end, the hub member defining a central longitudinal axis between the first and second hub ends; and
    a valve secured to the hub, the valve comprising a valve body including a first valve end terminating at a first end wall, a second valve end opposite the first end and terminating at a second end wall, and a valve passage extending through the valve body between the first and second end walls for accommodating a medical device introduced into the lumen of the hub member, the valve passage comprising a bore extending partially from the first end wall to a bottom surface at an intermediate region and defining a central bore axis extending from the first end wall to the intermediate region that is substantially parallel to and offset from the central longitudinal axis, the bore defining a side wall extending substantially parallel to the central bore axis from the first valve end towards the bottom surface, the valve passage further comprising a slit extending through the valve body from the bottom surface to the second end wall,
    wherein the valve passage further comprises a recess within the bore that has a larger cross-section than the bore.

10. The hub of claim 9, wherein the hub member comprises an outer wall, and wherein the bore is offset within the valve body such that the bore is closer to one side of the outer wall than the opposite side of the outer wall.

11. The hub of claim 10, wherein the one side of the outer wall includes a relatively thin walled region to facilitate slitting through the hub member and the valve.

12. The hub of claim 9, wherein the hub member comprises a first portion including the first hub end, and a second portion including the second hub end, and wherein the second portion is coupled to the first hub portion by a hub arm.

13. The hub of claim 9, wherein the valve body comprises one or more connectors for securing the valve to the hub member.

14. The hub of claim 9, wherein the slit has a width perpendicular to the central longitudinal axis that extends partially between the one side of the outer surface of the valve body and the opposite side of the outer surface.

15. A hub for a sheath, catheter, or other tubular device, comprising:
   a hub member comprising a first hub end, a second hub end comprising one or more connectors for connecting the second hub end to an elongate tubular member sized for introduction into a patient's body, and a lumen extending therebetween for receiving a medical device introduced into the first hub end, the hub member defining a central longitudinal axis between the first and second hub ends, the first hub end comprising an outer wall including a relatively thin walled region extending substantially parallel to the longitudinal axis on one side of the outer wall that is thinner than an opposite side of the outer wall; and
   a valve comprising a valve body secured to the hub and a valve passage extending therethrough for accommodating a medical device introduced into the lumen of the hub member, the valve passage comprising a bore extending at least partially through the valve body from a first end wall to a bottom surface at an intermediate region and defining a central bore axis that is substantially parallel to and offset from the central longitudinal axis such that the bore is closer to the relatively thin walled region of the outer wall than the opposite side of the outer wall, the bore defining a side wall extending substantially parallel to the central bore axis from the first end wall towards the bottom surface,
   wherein the valve passage further comprises a recess within the bore that has a larger cross-section than the bore.

16. The hub of claim 15, wherein the thickness of the valve body adjacent the relatively thin walled region is thinner than the thickness of the valve body adjacent the region of the outer wall opposite the relatively thin walled region.

17. The hub of claim 15, wherein the hub and the valve body comprise cooperating features for aligning the thin walled region of the first hub end closer to the bore when the hub and valve body are attached together.

18. The hub of claim 15, wherein the bore extends partially through the valve body from the first end wall of the valve body towards a second end wall of the valve body to an intermediate region, the valve passage further comprising a slit extending through the valve body from the intermediate region to the second end wall.

19. A valve for a hub of a sheath, catheter, or other tubular device, comprising:
   a valve body comprising a first end terminating at a first end wall, a second end opposite the first end and terminating at a second end wall, a longitudinal axis extending between the first and second end walls, and an outer surface extending between the first and second end walls; and
   a valve passage extending through the valve body between the first and second end walls, the valve passage comprising a bore extending partially through the valve body from the first end wall to a bottom surface at an intermediate region, the bore defining a side wall extending from the first end towards the bottom surface defining a diameter smaller than the outer surface of the valve body, and a slit extending through the valve body from the bottom surface to the second end wall,
   wherein the bore defines a central axis that is substantially parallel to and offset from the longitudinal axis such that one side of the bore is closer to the outer surface of the valve body than the opposite side of the bore,
   wherein the valve passage further comprises a recess within the bore that has a larger cross-section than the bore.

* * * * *